US005101819A

United States Patent [19]

Lane

[11] Patent Number: 5,101,819

[45] Date of Patent: Apr. 7, 1992

[54] METHOD FOR INDUCING HYPOXIA AT LOW SIMULATED ALTITUDES

[76] Inventor: John C. Lane, 8134 Cayuga Trail East, Jacksonville, Fla. 32244

[21] Appl. No.: 728,603

[22] Filed: Jul. 11, 1991

[51] Int. Cl.[5] .......... A61M 16/00

[52] U.S. Cl. .......... 128/204.18; 128/205.26

[58] Field of Search .......... 128/202.12, 202.13, 128/202.16, 205.26; 73/865.6; 600/21

[56] References Cited

U.S. PATENT DOCUMENTS

| | | | |
|---|---|---|---|
| 1,827,530 | 10/1931 | Le Grand | 128/202.12 |
| 2,373,333 | 4/1945 | Onge | 128/202.12 |
| 3,536,370 | 10/1970 | Evans et al. | 73/865.6 |
| 4,633,859 | 1/1987 | Reneau | 128/205.26 |
| 4,974,829 | 12/1990 | Gamow et al. | 128/200.12 |

OTHER PUBLICATIONS

"Recent Engineering Developments in Strato-Chambers" by J. G. Bergdoll, Jr., Journal of the American Society of Refrigerating Engineering, Jan. 1943, pp. 25-33.

*Primary Examiner*—Edgar S. Burr
*Assistant Examiner*—Aaron J. Lewis
*Attorney, Agent, or Firm*—Thomas C. Saitta

[57] ABSTRACT

A method and apparatus for inducing hypoxia in persons comprising a hypobaric chamber and means to introduce excess nitrogen into the atmosphere of the chamber, where hypoxia is induced by lowering the pressure within the chamber to a pressure equivalent to a high altitude, but less than 18,000 feet, and introducing an excess amount of nitrogen gas into the chamber, thus lowering the partial pressure of oxygen within the chamber.

2 Claims, 1 Drawing Sheet

METHOD FOR INDUCING HYPOXIA AT LOW SIMULATED ALTITUDES

BACKGROUND OF THE INVENTION

The invention relates generally to the field of methods and means for inducing hypoxia symptoms in persons undergoing altitude flight training. More particularly, the invention relates to methods and means for inducing hypoxia by producing an enriched nitrogen and depleted oxygen atmosphere at moderately reduced pressures and in relatively short time frames in hypobaric chambers.

Hypoxia resulting from atmospheric oxygen partial pressures lower than normal can occur during aircraft flights. Hypoxia may occur at altitudes at or greater than approximately 10,000 feet above sea level. The early symptoms indicate a possible impending loss of consciousness, and it is therefore imperative that persons learn to recognize the onset of hypoxia in time to take precautionary measures—e.g., utilize an auxiliary source of oxygen or decrease the altitude of the aircraft—to remain conscious. It is standard aviation physiology training practice to induce hypoxia symptoms by utilizing a hypobaric chamber to reduce the internal atmospheric pressure, and thus the partial pressure of oxygen available to the trainees. For example, reduction of the atmospheric pressure within the chamber to approximately 5.46 psi matches the pressure to be encountered at an altitude of 25,000 feet above sea level. At this pressure the partial pressure of oxygen in the atmosphere within the chamber is low enough to induce hypoxia symptoms in the trainees. Because exposure to this low pressure will have to be maintained for a time period sufficient to induce the hypoxia symptoms, there is a significant documented risk of causing decompression sickness in the trainees. Pressures equivalent to greater than 18,000 feet above sea level create this potential for decompression sickness.

To reduce the risk of decompression sickness, routine practice includes a thirty minute pre-breathing period of oxygen, but this preventative method is not always successful. Additionally, the use of 100 percent oxygen is required within the chamber during the simulated ascent and descent.

It is important in training that conditions to be encountered in the real environment are simulated as accurately as possible. Thus the preferred method is to use a hypobaric chamber to provide reduced pressure and reduced oxygen partial pressure to the trainees, rather than merely reducing the oxygen content alone by breathing a low oxygen mixture through an oronasal mask. The lower pressure more accurately reflects the conditions encountered at high altitude and addresses other training objectives, such as practicing the valsalva maneuver. However, the concurrent incidents of decompression sickness accompanying this method create a loss of man-hours and result in significant medical expenditures.

It is an object of this invention to provide a method and means for inducing hypoxia symptoms without exposing the trainees to pressures equivalent to those encountered at greater than 18,000 feet above sea level, thus removing the risk of decompression sickness.

It is a further object to provide such a method and means which expose the trainees to a low pressure situation concurrent with an oxygen depleted atmosphere, such that the hypoxia demonstration will be realistic.

It is a further object to provide a method and means which can be utilized through changes made to existing hypobaric chambers.

SUMMARY OF THE INVENTION

The invention comprises a method and means for inducing hypoxia symptoms in persons training in hypobaric chambers, where the pressure within the chamber is maintained well above the pressure at which decompression sickness can occur. In particular, the method comprises reducing pressure within the chamber below that of ambient but not exceeding the pressure at which decompression sickness occurs, and simultaneously creating low oxygen conditions within the chamber sufficient to induce hypoxia symptoms, through the addition of excess nitrogen into the chamber atmosphere.

The method comprises providing a hypobaric chamber having atmosphere control means capable of producing a nitrogen enriched atmosphere within the chamber. During the training, the chamber pressure is reduced to the equivalent of the pressure at an altitude of less than 18,000 feet, such as 10,000 feet for example. The atmosphere control means then creates a nitrogen enriched atmosphere within the chamber such that a greater than normal nitrogen to oxygen ratio is present. An approximately 85 percent nitrogen—15 percent oxygen atmospheric composition at 10.1 psi, the pressure found at 10,000 feet, produces a situation equivalent to the partial pressure of oxygen encountered at 25,000 feet, which has a pressure of only 5.5 psi, and will induce hypoxia in the trainees. This pressure equivalent to 10,000 feet is well below the 18,000 feet threshold for possible decompression sickness.

The enriched nitrogen atmosphere can be created within the hypobaric chamber by several methods, all of which involve the addition of excess nitrogen into the chamber. A semi-permeable membrane can be used to selectively filter and separate ambient air to create a supply of excess nitrogen, or a nitrogen generator or tanks of compressed nitrogen can directly supply an excess of nitrogen into the chamber to alter the atmospheric composition. All three means are readily and easily adaptable to existing hypobaric chambers.

DETAILED DESCRIPTION OF THE INVENTION

Figure 1:
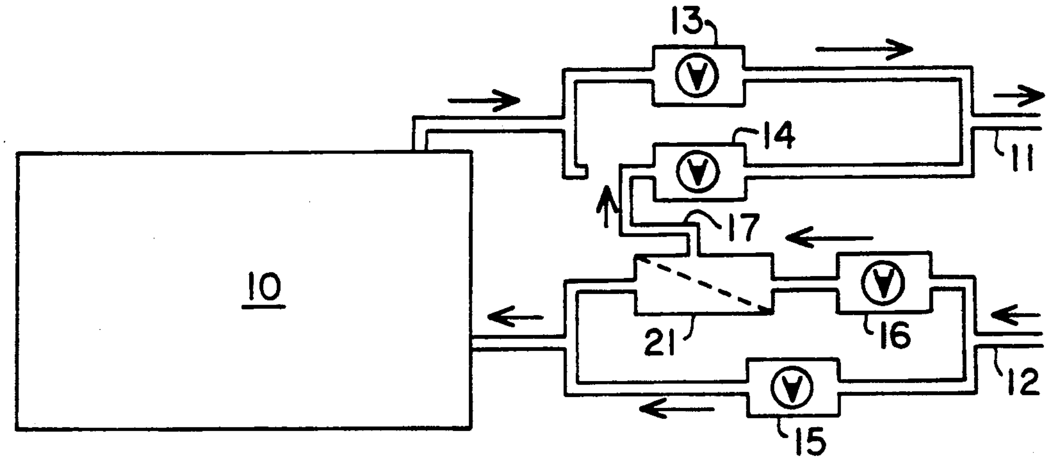
FIG. 1 illustrates a hypobaric chamber adapted with an atmosphere control means comprising a semi-permeable membrane system.

The invention comprises methodology and means to induce hypoxia symptoms in trainees inside a hypobaric chamber at a pressure level well above the pressure threshold at which decompression sickness becomes a risk factor. Hypobaric chambers are well known, and comprise a controlled, sealable environment within which the atmospheric pressure can be manipulated to create a low pressure environment within the chamber.

The chamber can therefore be used at ground level to simulate pressure conditions encountered in flight, since pressure decreases as altitude increases. The reduced pressure is achieved by evacuating atmospheric gases from the chamber. To return the chamber to ambient pressure, atmospheric gases are reintroduced.

Evacuation of the atmosphere to achieve the decreased pressure results in a decrease in the available oxygen for human consumption. Beyond a critical point, there is not enough oxygen available to sustain consciousness. To train aircrews to recognize the early symptoms of oxygen deprivation, i.e., hypoxia, the hypobaric chambers are used in aviation physiology training programs. A standard procedure is to lower the internal chamber pressure to a pressure equivalent to that encountered at 25,000 feet above sea level—a change from the 14.7 psi found at sea level to the 5.5 psi encountered at 25,000 feet. At pressures equivalent to 18,000 feet or more above sea level, however, the possibility exists for the trainees to suffer decompression sickness.

The basis for the calculations used in the method stem from Dalton's Law and the known atmospheric percentages, here illustrated using a target simulated atmospheric environment of 25,000 feet and an internal hypobaric chamber pressure equivalent to 10,000 feet:

| Pb | | = | $PO_2$ | + | $PN_2$ | + | $PCO_2$ | + | PAR |
|---|---|---|---|---|---|---|---|---|---|
| Atmospheric Vol % | | = | 20.95 | | 78.08 | | .03 | | .93 |
| Sea Level | 759.97 mmHg | = | 159.21 | | 593.38 | | .23 | | 7.07 |
| 10,000 Feet | 522.73 mmHg | = | 109.51 | | 408.15 | | .16 | | 4.86 |
| 25,000 Feet | 282.45 mmHg | = | 59.17 | | 220.54 | | .08 | | 2.63 |

Solving for alveolar volume percentages given constant $PaH_2O$ and experimentally measured $PaO_2$, and $PaCO_2$, gives:

| Pb - 47 mmHg $PaH_2O$ | | = | $PaO_2$ | + | $PaN_2$ | + | $PaCO_2$ | + | PaAR |
|---|---|---|---|---|---|---|---|---|---|
| Sea Level | 712.97 mmHg | = | 103.0 | | 563.19 | | 40.0 | | 6.78 |
| Alveolar Vol % | | = | 14.45 | | 78.99 | | 5.61 | | .95 |
| 10,000 Feet | 475.73 mmHg | = | 61.2 | | 375.02 | | 35.0 | | 4.51 |
| Alveolar Vol % | | = | 12.86 | | 78.83 | | 7.36 | | .95 |
| 25,000 Feet | 235.45 mmHg | = | 30.4 | | 175.94 | | 27.0 | | 2.11 |
| Alveolar Vol % | | = | 12.91 | | 74.72 | | 11.47 | | .90 |

The alveolar gas equation is:

The alveolar gas equation is:

$$PaO_2 = (Pb - PH_2O)FIO_2 - PaCO_2\left(FIO_2 + \frac{1 - FIO_2}{R}\right)$$

where:

$PaO_2$ is the mean alveolar oxygen pressure at 25,000 ft.

Pb is the ambient barometric pressure at 10,000 ft.

$PH_2O$ is the water vapor pressure at body temperature $FIO_2$ is the fraction of inspired oxygen $PaCO_2$ is the mean alveolar $CO_2$ pressure at 10,000 ft.

R is the respiratory exchange ratio at 10,000 ft.

Solving the alveolar gas equation for the $FIO_2$ which would simulate 25,000 feet at a pressure altitude of 10,000 feet gives a required fraction of inspired oxygen $FIO_2=0.1444$. In other words, inspiration of a 14.5% by volume oxygen atmosphere while at a 10,000 feet pressure altitude will result in an alveolar partial pressure of oxygen normal to a pressure altitude of 25,000 feet. Nitrogen enrichment from the standard 78% atmospheric volume to 85% atmospheric volume is used to supplant the depleted oxygen. Since the increased percentage of nitrogen is breathed at a reduced atmospheric pressure in the chamber, the partial pressure of nitrogen is still less than that normal to sea level and is therefor not harmful.

To summarize in a tabular format:

| Simulating 25,000 ft. | Pb | = | $PO_2$ | + | $PN_2$ | + | $PCO_2$ | + | PAR |
|---|---|---|---|---|---|---|---|---|---|
| at 10,000 ft. | 522.73 mmHg | = | 75.48 | | 442.23 | | .16 | | 4.86 |
| Atmospheric Volume % | | = | 14.44 | | 84.60 | | .03 | | .93 |
| Pb - 47 mmHg $PaH_2O$ | | = | $PaO_2$ | + | $PaN_2$ | + | $PaCO_2$ | + | PaAR |
| 475.73 mmHg | | = | 30.4 | | 405.82 | | 35.0 | | 4.51 |
| Alveolar Volume % | | = | 6.39 | | 85.3 | | 7.36 | | .95 |

Obviously, the method can be used with any chosen simulated altitude pressure and any chosen hypobaric chamber internal pressure, provided the correct amount of nitrogen is introduced into the chamber. The percentage of nitrogen will be directly related to the chosen simulated pressure and the chosen internal pressure. The general formula to calculate the fraction of inspired nitrogen required to induce the alveolar partial pressure of oxygen normal to a given altitude, under standard atmospheric conditions, is as follows:

$$FIN_2 = 1 - FIO_2 = 1 - \frac{PaO_2 + \frac{PaCO_2}{R}}{Pb - PH_2O - PaCO_2 + \frac{PaCO_2}{R}}$$

Where:

$FIN_2$ is the fraction of inspired $N_2$ after enrichment $FIO_2$ is the fraction of inspired $O_2$ after displacement $PaO_2$ is the mean alveolar partial pressure of $O_2$ normal, under standard atmospheric conditions, to the altitude selected for simulation at a lower altitude in the hypobaric chamber $PaCO_2$ is the mean alveolar partial pressure of $CO_2$ at the pressure altitude selected for the chamber R is the respiratory exchange ratio at the pressure altitude selected for the chamber Pb is the barometric pressure at the pressure altitude selected for the chamber $PH_2O$ is the constant alveolar partial pressure of $H_2O$ vapor at body temperature To practice the method, a hypobaric chamber is outfitted with means to control the nitrogen to oxygen ratio of the atmosphere within the chamber. The atmosphere control means is used to achieve the desired percentage by volume oxygen atmosphere within the chamber during the hypoxia training. The trainees enter the hypobaric chamber and the internal environment is evacuated to a pressure equivalent to an altitude of up to 18,000 feet. A pressure equivalent to that of 10,000 feet, i.e., 10.1 psi, is preferred, since it is at this altitude that hypoxia can occur during actual flights, but this pressure is still well above the pressure at which decompression sickness occurs. The persons within the chamber thereby experience the effects of an atmospheric pressure lower than ambient, an experience which correlates to increased altitude in an aircraft. The atmosphere control means are then used to enrich the internal atmosphere within the hypobaric chamber by increasing the nitrogen percentage such that an overall volume percentage for nitrogen in excess to that found at ambient is obtained. The exact amount of nitrogen enrichment necessary will be a function of the internal chamber pressure chosen and the simulated altitude chosen. Higher internal chamber pressures, those equivalent to low altitudes, will require greater excess nitrogen amounts to achieve the hypoxia symptoms, while lower internal pressures, those equivalent to higher altitudes, will require smaller excess nitrogen amounts. From the example solved for above, an internal atmosphere of approximately 85.5% nitrogen and approximately 14.5% oxygen at a pressure equivalent of 10,000 feet will simulate within the chamber the partial pressure of oxygen to be encountered at 25,000 feet above sea level. Standard measuring gauges and techniques are utilized to monitor the inflow of nitrogen and the internal atmosphere. Within minutes, the trainees will experience the symptoms of hypoxia due to the decreased oxygen and can thus learn to take steps to prevent loss of consciousness in a real situation, e.g., inhaling oxygen through a breathing mask. After the demonstration, the atmosphere and the pressure within the chamber is returned to normal.

A typical hypobaric chamber 10, as shown generally in the figures, has a large sealable area of suitable size to allow one or more individuals to enter the internal area. Once persons enter into the chamber 10 and seal off the chamber 10 from the external atmosphere, the internal atmosphere within the chamber 10 is withdrawn by means of a vacuum line 11 connected to a pump. Since the resulting drop in internal chamber 10 pressure is equivalent to increasing altitude in an aircraft, this is the equivalent of a climb. The amount of atmosphere removed from the chamber 10 is controlled through use of a climb control valve 13 and climb throttle 14, mounted parallel in the vacuum line 11, the climb control valve 13 being used for gross adjustments and the climb throttle 13 being used for finer adjustments of internal pressure. To increase the pressure within the chamber 10 after a demonstration, the equivalent of diving an aircraft, external ambient air is introduced into the chamber 10 through inbleed line 12, controlled by parallel mounted dive control valve 15 and dive throttle 16. Upon return to ambient pressure within the chamber 10, it is unsealed for egress by the trainees.

A chamber 10 capable of producing hypoxia with the method disclosed above can be constructed by altering the structure of a standard hypobaric chamber 10. One embodiment of a hypobaric chamber 10 adapted to provide a nitrogen enriched atmosphere at reduced pressure comprises the incorporation of a selectively permeable membrane separator system 21 into the inbleed line 12, as shown in FIG. 1. Such membrane separator systems 21 are well known. The separator system 21 consist of bundles of semipermeable membranes formed into tiny hollow fibers. Thousands of these hollow fibers in each separator provide maximum separation area in a compact module. As pressurized air flows into the fibers, the faster gases, such as oxygen, water, and carbon dioxide, permeate through the fiber walls and are collected at reduced pressure and removed through a connector line 17 connected to the vacuum line 11 and controlled by the climb throttle 14, which is now no longer fed by the internal atmosphere within the chamber 10 as in a standard hypobaric chamber, the ingress line to the climb throttle 14 having been cut and sealed. The non-permeate gas, nitrogen, exits from the fiber bundles at the end of the separator 21 at the same pressure as the entering air and is drawn into the internal chamber 10 through the inbleed line 12 because of the reduced internal pressure.

Figure 2:
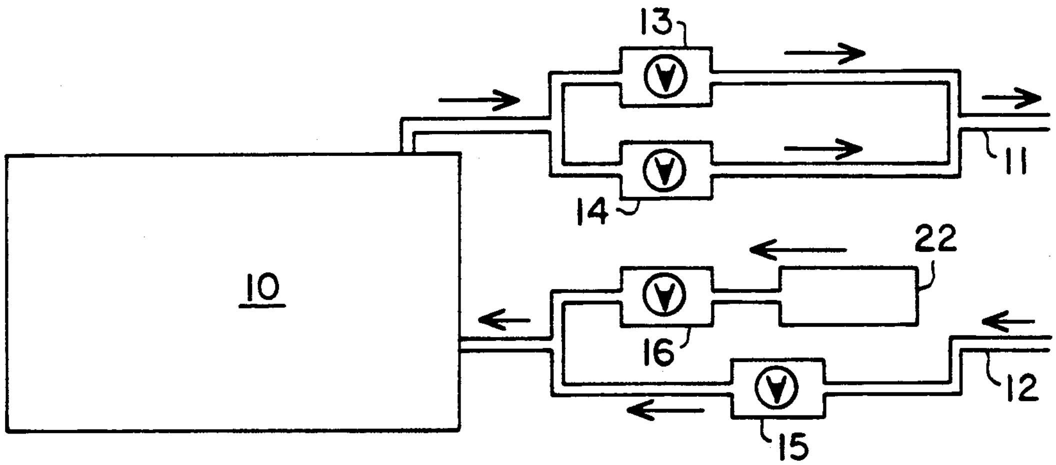
FIG. 2 illustrates a hypobaric chamber adapted with an atmosphere control means comprising a nitrogen generator system.
Figure 3:
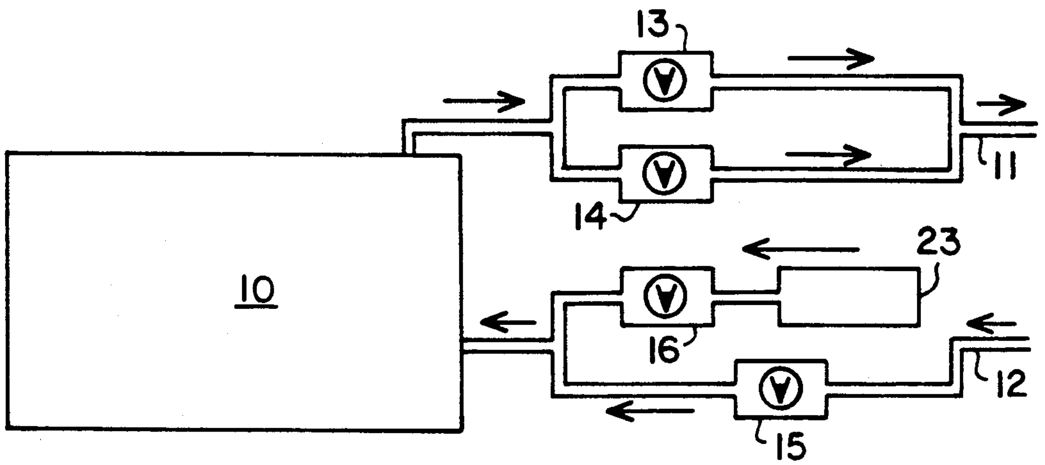
FIG. 3 illustrates a hypobaric chamber adapted with an atmosphere control means comprising a compressed nitrogen supply means.

In a second embodiment, as shown in FIG. 2, a nitrogen generator system 22, of any type known in the art capable of producing a sufficient quantity of nitrogen, is connected to the inbleed line 12 so as to be controlled by the dive throttle 16, such that operation of the dive throttle 16 allows nitrogen to be introduced directly into the chamber 10. The dive throttle 16 is here disconnected from the inbleed line 12 by cutting and sealing the standard ingress line so that only the dive control valve 15 controls the ingress of ambient atmosphere through inbleed line 12. In a third embodiment, shown in FIG. 3, compressed nitrogen supply means 23, such as a tank of compressed nitrogen, is connected through the dive throttle 16 in the same manner. It is of course also possible to alter standard hypobaric chambers by adding the atmosphere control means—the permeable membrane separator system, the nitrogen generator or the nitrogen tanks—and providing separate controls and input lines.

To operate the hypobaric chamber 10 to achieve a hypoxia demonstration, the operator, after the trainees are in the hypobaric chamber 10 and it is sealed, opens the climb control valve 13 to remove atmosphere from inside the chamber 10 and thus reduce the internal pressure to the equivalent of the pressure found at the desired simulated altitude below 18,000 feet. The operator then initiates the introduction of nitrogen into the chamber 10 to create the nitrogen enriched atmosphere by opening the dive throttle 16. The nitrogen from the semi-permeable membrane separator system 21, the nitrogen generating system 22 or the compressed nitrogen supply means 23 is then drawn into the chamber 10 by the pressure differential. When the internal atmosphere achieves the calculated volume percentage ratio of nitrogen to oxygen, the dive throttle is closed. The operator can maintain the simulated altitude and pressure at no variance by opening the climb throttle 14 slightly to balance the ingress of excess nitrogen into the chamber 10. The internal atmospheric environment in terms of breathable gases within the chamber 10 is now equivalent, regarding the partial pressure of oxygen, to that encountered at the target altitude of more than 18,000 feet above sea level without the presence of potentially damaging extreme low pressure and the risk of causing decompression sickness. Upon finishing the hypoxia demonstration, the chamber 10 is returned to ambient pressure by opening the dive control valve 15 to allow ambient air into the chamber.

It may be obvious to those skilled in the art to utilize equivalents and substitutions for the above described components of the invention, and the examples given are by way of illustration only. The true scope and definition of the invention is to be as set forth in the following claims.

I claim:

1. A method for inducing high altitude hypoxia symptoms in persons undergoing flight training in hypobaric chambers without exposing such persons to extreme low pressure capable of causing decompression sickness, comprising:

(A) providing a hypobaric training chamber capable of pressure reduction ranging from ambient pressure to pressures equivalent to higher altitudes;

(B) providing means to produce a nitrogen enriched atmosphere in said hypobaric chamber by introducing nitrogen into said hypobaric chamber, whereby the percentage of nitrogen in said atmosphere is greater than the percentage occurring at ambient pressure;

(C) reducing the pressure within said hypobaric chamber to the pressure equivalent to an altitude of no more than 18,000 feet above sea level;

(D) introducing nitrogen into said hypobaric chamber to produce a nitrogen enriched atmosphere within said hypobaric chamber whereby the percentage of nitrogen in said atmosphere is greater than the percentage occurring at ambient pressure, where the percentage of nitrogen in said chamber is a calculated amount related to the reduced pressure within said chamber to simulate oxygen partial pressures encountered at altitudes of greater than 18,000 feet above sea level;

(E) maintaining said pressure equivalent and nitrogen enriched atmosphere in said hypobaric chamber until hypoxia symptoms occur to persons in said hypobaric chamber.

2. The method of claim 1, where said pressure within said hypobaric chamber is reduced to a pressure equivalent to the pressure encountered at an altitude between 10,000 and 18,000 feet above sea level.

* * * * *